United States Patent [19]
Durand et al.

[11] 3,945,122
[45] Mar. 23, 1976

[54] THREE DIMENSIONAL NUMERICAL SURFACE DESCRIPTOR

[75] Inventors: Philip E. Durand, Hudson;
Lawrence R. McManus, Lynn;
William D. Claus, Jr., Natick, all of Mass.

[73] Assignee: The United States of America as represented by the Secretary of the Army, Washington, D.C.

[22] Filed: Oct. 29, 1974

[21] Appl. No.: 518,929

[52] U.S. Cl............................ 33/174 D; 33/174 PA
[51] Int. Cl.²........................................ G01B 5/20
[58] Field of Search ............ 33/174 D, 174 PA, 175

[56] References Cited
UNITED STATES PATENTS

| | | | |
|---|---|---|---|
| 788,362 | 4/1905 | Lavery | 33/174 D |
| 1,023,542 | 4/1912 | Winter | 33/174 D |
| 1,897,941 | 2/1933 | Lavery | 33/174 D |

FOREIGN PATENTS OR APPLICATIONS

| | | | |
|---|---|---|---|
| 3,167 | 9/1873 | United Kingdom | 33/175 |

*Primary Examiner*—Richard E. Aegerter
*Assistant Examiner*—Richard R. Stearns
*Attorney, Agent, or Firm*—Nathan Edelberg; Robert P. Gibson; Charles C. Rainey

[57] ABSTRACT

An apparatus for the measurement and numerical description of three-dimensional objects, such as human heads. The apparatus comprises a hollow hemisphere having a plurality of probes which can be moved toward or away from a three-dimensional object held in place within the hollow hemisphere. The probes are movable in sleeves which pass through the wall of the hemisphere, enabling the measurement of distances between the hemisphere and the three-dimensional object at various points on the outer surface thereof.

3 Claims, 3 Drawing Figures

THREE DIMENSIONAL NUMERICAL SURFACE DESCRIPTOR

The invention described herein may be manufactured, used, and licensed by or for the Government for governmental purposes without the payment to us of any royalty thereon.

BACKGROUND OF THE INVENTION

This invention relates to an apparatus for the measurement and numerical description of a head or other three-dimensional object.

In the making of head measurements in accordance with standard anthropometric methods it has been customary to measure such characteristics as the circumference, length, breadth, and height of heads, using calipers and tape measures. From these measurements heads have been categorized into various sizes. This has certain shortcomings since there are so many different combinations of the more common anthropometric features of heads in a large population of men.

For the development of the most efficient ballistic protective helmets for use by infantry soldiers as well as other military personnel it has become important to find new ways of measuring and characterizing heads so that the most efficient shape and dimensions can be incorporated in the smallest number of different helmets, thus reducing logistic problems to a minimum while providing maximum safety and comfort. It is of little value from a military standpoint to provide helmets of excellent ballistic resistance if soldiers are going to abandon their helmets when they find themselves in a very difficult military situation where a slight interference with critical combat actions may spell the difference between survival and death. Innumerable helmets have been discarded when they were most needed because of either actual or fancied interference with the firing of a rifle or other combat problems attributed to the helmets made in accordance with prior designs and methods.

It is, therefore, an object of the present invention to provide an apparatus for measuring and numerically describing heads to enable the designing of better fitting and more effective helmet shapes and sizes, particularly for military personnel.

A further object is to provide an apparatus for measuring and numerically describing a wide variety of three-dimensional objects, including feet, torso, and other portions of the anatomy, or even inanimate three-dimensional objects.

Other objects and advantages will appear from the following description, and the novel features will be particularly pointed out in connection with the appended claims.

SUMMARY OF THE INVENTION

The apparatus comprises a hemisphere on which are mounted cylindrically shaped probes which are movable toward and away from a common point within a three-dimensional object, such as a human head. The hemisphere is supported at the front and rear thereof by means adjustably mounted on supporting posts so that the height and tilt of the hemisphere are adjustable. Once the height and orientation of the hemisphere have been set and the apparatus clamped in place in the desired position with respect to the head of a subject, the probes are moved one by one until they contact the surface of the head of different locations. The distances from the inner surface of the hemisphere to the surface of the head at the various points are determined from the lengths of the probes outside of the hemisphere and therefrom the lengths inside the hemisphere. These values are converted to spherical coordinates to describe the surface of the head so that a model of the head can be produced and used in the design of protective helmets.

A large number of subjects can be similarly measured and the resulting measurements can be converted statistically to an unlimited number of sizes of headforms and helmet sizes each suitable for relatively large numbers of different human heads.

DESCRIPTION OF THE PREFERRED EMBODIMENT

Figure 1:
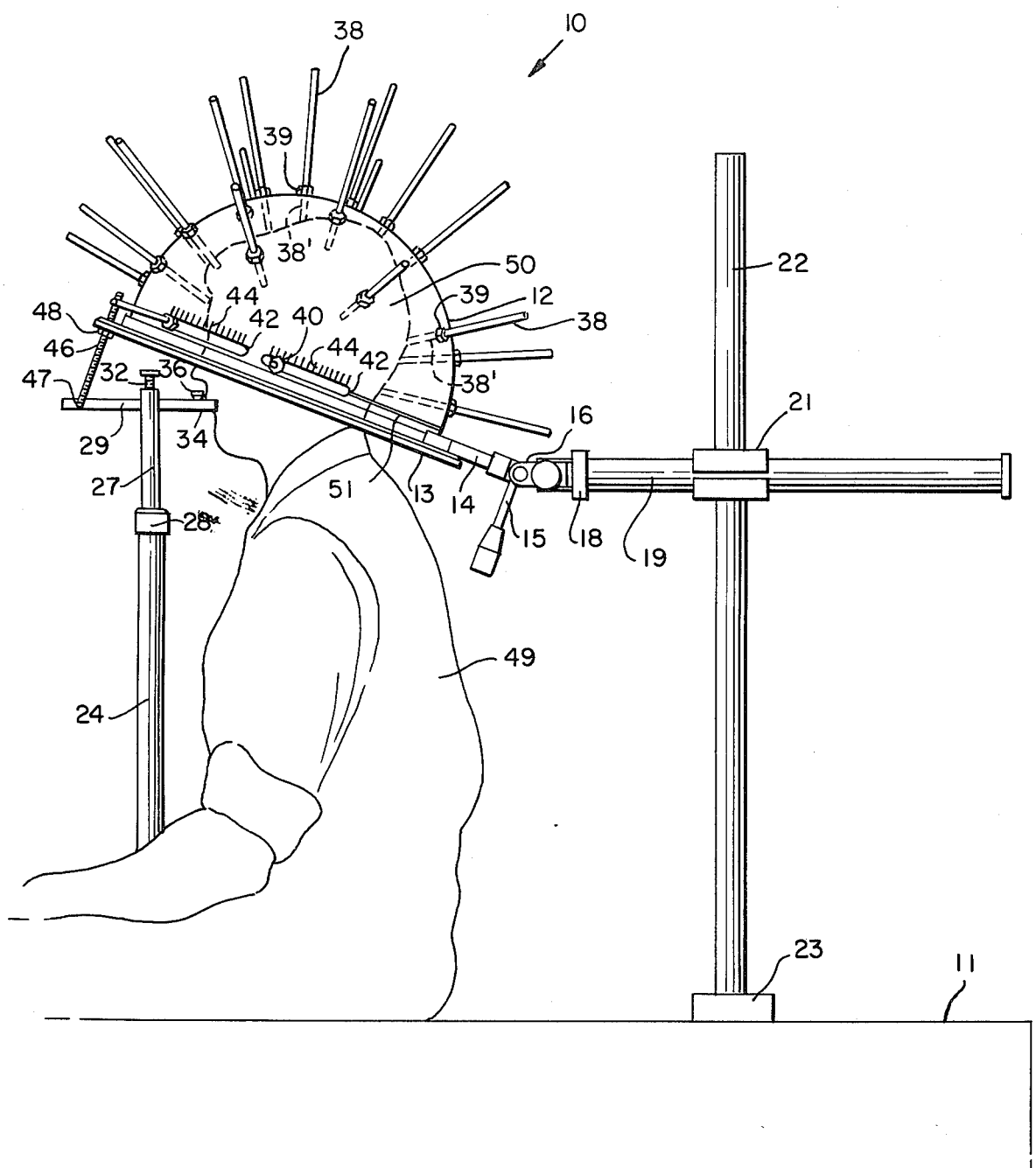
FIG. 1 is a side elevation view of the three dimensional numerical surface descriptor and a human subject seated on a platform supporting the descriptor in position for the measurement of the subject's head.
Figure 2:
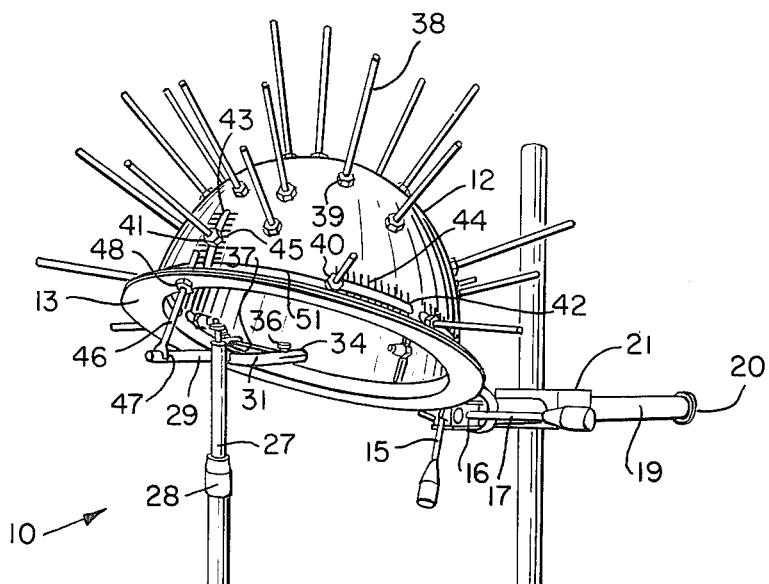
FIG. 2 is a perspective view of the three dimensional numerical surface descriptor mounted on a platform, but without a subject associated therewith.
Figure 3:
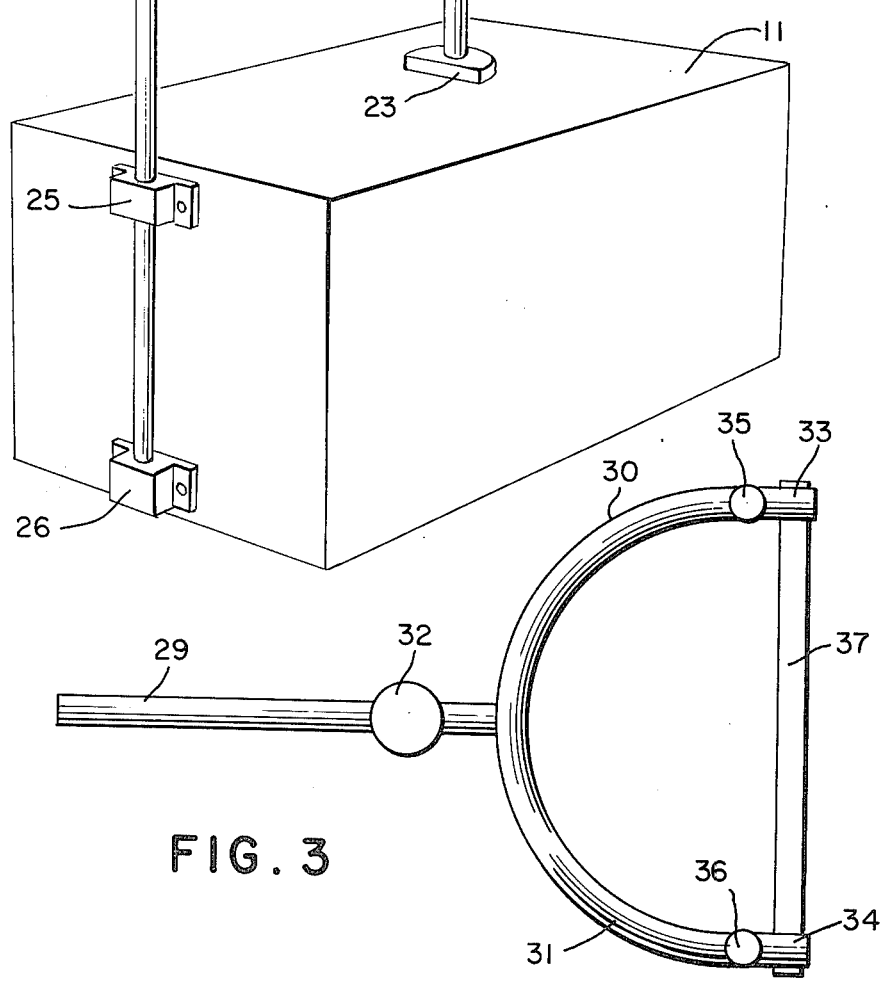
FIG. 3 is a plan view of the bite bar support with bite bar clamped thereby as viewed from above when it is in its normal operating position.

The preferred embodiment of the invention is shown in the drawings and involves a hollow hemisphere having a plurality of probes associated therewith which can be moved toward or away from a three-dimensional object held in place within the hollow hemisphere so that measurements may be made of the distances between the hemisphere and the three-dimensional object at various points on the outer surface thereof.

Referring to the drawing, reference numeral 10 represents generally the three dimensional numerical surface descriptor which is mounted on a platform 11 suitable for supporting a subject 49 in a sitting position with his head 50 largely within hemisphere 12, which is hollow. The hemisphere is preferably made of clear, transparent plastic and is mounted on a flange-like rim 13, which is preferably made of metal, such as aluminum or an aluminum alloy. Bracket 14 is attached to rim 13 and has a set screw 15 for adjustably clamping it to bracket 16, which has a set screw 17 for adjustably clamping bracket 16 with the assistance of collar 18 to horizontal rod 19, thus providing universal adjustability to the hemisphere. Horizontal rod 19 has a flanged end 20 which acts as a stop when horizontal rod 19 is pushed or slid forward through clamp 21, the latter serving as a means for adjustably clamping horizontal rod 19 to vertical rear rod 22, which is attached by base support bracket 23 to the upper surface of platform 11. Clamp 21 is held by a plurality of set screws (not shown) clamped to both horizontal rod 19 and vertical rear rod 22. Telescoping vertical front shaft 24 is attached to the front end of platform 11 by means of upper bracket 25 and lower bracket 26. Telescoping vertical front shaft 24 has an upper telescopic element 27 which may be clamped extended or retracted to varying extents by means of rotating clamp 28, which clinches the split end of the barrel of vertical front shaft 24 around upper telescopic element 27 when rotating clamp 28 is turned clockwise on shaft 24. Upper telescopic element 27, in cooperation with vertical front shaft 24, supports bite bar support 29 at various heights depending on the torso height of the subject 49. Bite bar support 29 has a left tine 30 and a right tine 31 and a straight rod-like portion which passes through a hole through the upper end of upper telescopic element 27 to which bite bar support 29 is clamped by set screw 32. Left tine 30 has a clamp 33 at its free end and right tine 31 has a clamp 34 at its free end, clamp 33 being tightened or loosened by set screw 35 and clamp 34 being similarly tightened or loosened by set screw 36 so that bite bar 37, which is a flat plate-like element, such as a tongue depressor, is held tightly clamped between clamps 33 and 34 on the two ends of the tines of bite bar support 29 when the descriptor is in use. The tilt of the hemisphere from front to rear and from side to side is controlled by means of brackets 14 and 16 and set screws 15 and 17. To help support the hemisphere in position after it has been properly adjusted with respect to height and tilt, front support rod 46 is adjusted in length by resting the forked end 47 thereof against the top of bite bar support 29 and moving adjusting nut 48 along the threaded end of rod 46 to a position directly under and against the lower surface of rim 13 of the hemisphere. The hemisphere is provided with 27 cylindrical probes 38 (designated 38' in phantom on the inside of hemisphere 12) which pass through the walls of the hemisphere by sliding in sleeves, preferably made of metal, of which there are fixed sleeves 39, horizontally adjustable sleeves 40, and vertically adjustable sleeves 41. The probes 38 are preferably solid rods, but may be hollow, if desired. The horizontally adjustable sleeves 40 move in horizontal sleeve adjusting slots 42, which pass through the walls of the hemisphere and which permit the probes which pass through sleeves 40 to be adjusted horizontally to bring them into alignment with the subject's canthi. The vertically adjustable sleeves 41 move in vertical sleeve adjusting slots 43, which pass through the walls of the hemisphere along the polar plane of the hemisphere. Each of the sleeves is provided with a locking nut to lock the sleeve in place when it is in the proper position for the cylindrical probe operating therein to contact a selected point on the surface of head 50. The hemisphere has horizontal angular graduations 44 along the upper rims of the horizontal sleeve adjusting slots 42 and vertical angular graduations 45 along the side rims of the vertical sleeve adjusting slots 43. The hemisphere also has an equatorial plane indicator 51 etched in its surface or otherwise marked on the exterior surface of the hemisphere to assist in alignment of the hemisphere with respect to selected portions of the head of the subject.

OPERATION OF THE APPARATUS

In using the apparatus, a subject 49 is placed in a sitting position on platform 11 so that his head 50 is largely within hemisphere 12 and so that bite bar 37 is firmly grasped between his teeth with his head placed so that the Frankfort plane thereof is parallel to the ground. The Frankfort plane is the standard plane of orientation of the head, determined by locating the lower edges of the eye sockets and a single tragus in the same horizontal plane. Grasping the bite bar between the teeth after it has been properly adjusted for the particular subject substantially immobilizes the head so that it remains in the same position throughout the ensuing adjustments of the probes with respect to the surface of the subject's head and the measuring of the distances between the surface of the subject's head at strategically selected points and the inner wall of the hemisphere. The hemisphere is adjusted so that its polar plane is aligned coincidentally with the midsagittal plane of the subject's head and, therefore, passes through the front and rear vertical sleeve adjusting slots 43. The probe selected to represent the X-axis is a three-dimensional orthogonal coordinate system having X, Y, and Z axes is aligned with the subject's right tragus. The midsagittal plane, the right tragus, and the right external canthus of the subject's head are used to reference the head with respect to the equatorial plane and the polar plane of the hemisphere. The hemisphere is rotated so that the equatorial plane thereof includes the right tragus and the right external canthus of the subject. This orients the hemisphere with the equatorial plane at about an average (for various subjects) eighteen degree angle to the surface of the ground or the platform.

In the preferred embodiment there are nine probes in the polar plane of the hemisphere. Six of these are fixed while three are adjustable, two of the adjustable probes being at the rear of the hemisphere and the subject's head and one at the front of the hemisphere and the subject's head. There are nine probes on each side of the hemisphere from the polar plane, arranged at strategically selected points. The probes which are aligned with the tragi of the subject are at diametrically opposite positions on the hemisphere. They may be fixed, although in the drawing they are shown as adjustable. The probes which are aligned with the external canthi of the subject are adjustable because of the variations between different subjects.

When the hemisphere has been oriented with respect to the subject's head, as described above, the 27 probes are one by one pushed inwardly of the hemisphere until they touch the surface of the subject's head. The distance from the surface of the subject's head to the internal wall of the hemisphere is then measured with each probe by measuring the length of the probe extending outside of the hemisphere and, knowing the thickness of the wall of the hemisphere and any portion of the sleeve not included in the measurement of the length of the probe outside the hemisphere, such as thickness of nut 39 in each case, by difference from the total length of the probe arriving at the value of the distance from the surface of the subject's head to the internal wall of the hemisphere at that location. By subtracting the distance from the surface of the subject's head to the internal wall of the hemisphere from the known diameter of the hemisphere, one can arrive at the length of a ray from the center of the hemisphere to the surface of the subject's head at each of the 27 points selected for measurement. Knowing the positions of the probes in terms of three-dimensional coordinates and the lengths of the rays at each of 27 different points, the shape of the head can be numerically described so as to enable a model maker or sculptor to reproduce the shape of the head or other three-dimensional object subjected to similar measurement with the apparatus of the invention.

The apparatus of the invention has been described in terms of its use for measuring and describing the surface of a human head. However, it should be apparent that it may be used with any three-dimensional object which will fit inside of the hemisphere. Twenty-seven probes are preferably used to describe human heads in terms of twenty-seven points scattered over the surfaces of the heads. Other numbers of probes can, of course, be employed, depending on the type of three-dimensional object being described and how accurately the surface of the three-dimensional object needs to be described.

The hemisphere employed in the apparatus of the invention has been described as being preferably made of a clear, transparent plastic material. However, it may be constructed of opaque materials, if desired, since the distance from the inner surface of the hemisphere to the surface of the three-dimensional object is calculated from a measurement of the length of each probe outside of the hemisphere. The biggest problem involved in employing an opaque hemisphere would be in orienting the three-dimensional object within the hemisphere. This would be difficult with human heads if the hemisphere were not transparent, but might not be so difficult with certain other three-dimensional objects.

The apparatus of the invention is particularly useful in the measurement and description of human heads and in providing the basic information for designing improved helmets of different types. However, it may be adapted to the measurement and description of other three-dimensional objects, e.g. feet, torsos, etc.

It will be understood, of course, that various changes in the details, materials, and arrangements of parts, which have been herein described and illustrated, in order to explain the nature of the invention, may be made by those skilled in the art, within the principle and scope of the invention as expressed in the appended claims.

We claim:

1. An apparatus for the measurement and numerical description of a three-dimensional object which comprises, a hollow, transparent hemisphere, said hemisphere being sufficiently large to accommodate said three-dimensional object therein with space remaining between the outer surface of said three-dimensional object and the inner surface of said hemisphere, a plurality of cylindrically shaped solid rod probes, each of said probes fitting snugly in a sleeve extending through and lockably and unlockably attached to the wall of said hemisphere so that said probe is adapted to be moved inwardly and outwardly of said hemisphere, and means for adjustably supporting and clamping said hemisphere in a plurality of selected positions in relation to said three-dimensional object, whereby said probes may be moved inwardly of said hemisphere until they contact the outer surface of said three-dimensional object at a plurality of points and the distances from the inner surface of said hemisphere to the outer surface of said three-dimensional object at said plurality of points measured and converted into a numerical description of said three-dimensional object.

2. An apparatus according to claim 1, wherein said hemisphere is provided with a plurality of slots therein, each of said slots passing through said wall of said hemisphere, at least one of said sleeves and cooperating probe extending through each of said slots, said sleeves extending through each of said slots being lockably and unlockably attached to said wall of said hemisphere at selected locations along the slot.

3. An apparatus according to claim 2, wherein said hemisphere has means thereon for indicating the alignment of said hemisphere with respect to selected portions of the outer surface of said three-dimensional object.

* * * * *